(12) United States Patent
Suzuki

(10) Patent No.: US 7,663,016 B2
(45) Date of Patent: Feb. 16, 2010

(54) DISPOSABLE ABSORBENT SANITARY ARTICLE

(75) Inventor: Taichiro Suzuki, Tsurugi-cho (JP)

(73) Assignee: Livedo Corporation, Ehime (JP)

( * ) Notice: Subject to any disclaimer, the term of this patent is extended or adjusted under 35 U.S.C. 154(b) by 0 days.

(21) Appl. No.: 10/592,854

(22) PCT Filed: Mar. 11, 2005

(86) PCT No.: PCT/JP2005/004864

§ 371 (c)(1),
(2), (4) Date: Sep. 13, 2006

(87) PCT Pub. No.: WO2005/087162

PCT Pub. Date: Sep. 22, 2005

(65) Prior Publication Data

US 2007/0142802 A1    Jun. 21, 2007

(30) Foreign Application Priority Data

Mar. 15, 2004  (JP) ............................. 2004-072515

(51) Int. Cl.
*A61F 13/15* (2006.01)
*A61F 13/20* (2006.01)
(52) U.S. Cl. ...................................... 604/378; 604/367
(58) Field of Classification Search ......... 604/367–375, 604/378, 385.01
See application file for complete search history.

(56) References Cited

U.S. PATENT DOCUMENTS

| | | | |
|---|---|---|---|
| 4,055,180 A | 10/1977 | Karami | |
| 5,411,497 A | 5/1995 | Tanzer et al. | |
| 5,843,067 A | 12/1998 | Trombetta et al. | |
| 6,569,137 B2 | 5/2003 | Suzuki et al. | |
| 2001/0020157 A1 | 9/2001 | Mizutani et al. | |
| 2002/0095127 A1 | 7/2002 | Fish et al. | |
| 2002/0115969 A1* | 8/2002 | Maeda et al. | ............... 604/368 |

(Continued)

FOREIGN PATENT DOCUMENTS

EP    1 132 069    6/2001

(Continued)

*Primary Examiner*—Michele Kidwell
(74) *Attorney, Agent, or Firm*—Jordan and Hamburg LLP

(57) ABSTRACT

A disposable absorbent article 10 that includes an absorbent mat 13 between a liquid permeable top sheet 11 and a liquid impermeable back sheet 12, the absorbent mat 13 including a sheet-like water absorbent layer 15 that contains water absorbent resin powders 14 but that does not contain pulp fibers therein, and fiber assembly layers 17A and 17B each of which mainly consists of the pulp fibers 16, sequentially from the side of the top sheet 11, the sheet-like water absorbent layer 15 alternately including a plurality of water absorbent resin powder existing regions 15a, in each of which the water absorbent resin powders 14 are wrapped in two non-woven fabric sheets 20 and 21, and a plurality of water absorbent resin powder non-existing regions 15b, in each of which the water absorbent resin powders 14 are not wrapped in the two non-woven fabric sheets 20 and 21, in a width direction, wherein rising flaps 18 are provided on both sides of the sheet-like water absorbent layer 15, respectively. Bottom ends 18a of the rising flaps 18 are bonded to the top sheet 11 corresponding to the water absorbent resin powder non-existing regions 15b-1 and 15b-2 located on both lateral ends of the sheet-like water absorbent layer 15, respectively.

8 Claims, 3 Drawing Sheets

U.S. PATENT DOCUMENTS

2004/0019342 A1* 1/2004 Nagasuna et al. ...... 604/385.01
2006/0184146 A1 8/2006 Suzuki

FOREIGN PATENT DOCUMENTS

| | | |
|---|---|---|
| JP | 3-121069 | 5/1991 |
| JP | 5-317362 | 12/1993 |
| JP | 2001-190581 | 7/2001 |
| JP | 2002-224161 | 8/2002 |
| JP | 2004-275225 | 10/2004 |
| WO | WO-01/89439 | 11/2001 |

* cited by examiner

DISPOSABLE ABSORBENT SANITARY ARTICLE

FIELD OF THE INVENTION

The present invention relates to a disposable absorbent article such as a disposable diaper or disposable pants.

BACKGROUND OF THE INVENTION

As an improvement of a conventional technology (see Japanese Laid-open Patent Application No. 2002-224161 or a pamphlet of International Publication No. 01/89439), the applicant of the present application proposed a disposable absorbent article as explained below (Japanese Patent Application No. 2003-67287; Japanese Laid-open Patent Application No. 2004-275225). As shown in FIG. 5, the absorbent article includes an absorbent mat 3 between a liquid permeable top sheet 1 and a liquid impermeable back sheet 2. In addition, the absorbent article is characterized in that the absorbent mat 3 includes a sheet-like water absorbent layer 5, which contains water absorbent resin powders 4, but does not contain pulp fibers therein, and fiber assembly layers 7A and 7B that include the water absorbent resin powders 4 and the pulp fibers 6, sequentially from a top sheet 1 side, and in that the sheet-like water absorbent layer 5 alternately includes water absorbent resin powder existing regions 5a, in each of which the water absorbent resin powders 4 are wrapped in, and water absorbent resin powder non-existing regions 5b, in each of which the water absorbent resin powders 4 are not wrapped in.

Said disposable absorbent article has the following advantages. The disposable absorbent article has a high absorbing performance that enables long-time use, hardly gets out of shape even after absorbing body fluid, and hardly causes backflow of body fluid so that the disposable absorbent article can make a wearer who wears the article feel comfortable.

Meanwhile, it can be considered that rising flaps 8 may be provided on both sides of the sheet-like water absorbent layer 5, respectively, and that bottom ends 8a of the respective rising flaps 8 are bonded to the top sheet 1 corresponding to water absorbent resin powder existing regions 5a-1 and 5a-2 of the sheet-like water absorbent layer 5 with an adhesive 9 or the like.

However, in each of the water absorbent resin powder existing region 5a, when the water absorbent resin powders 4 repeatedly absorb urine and then being swelled, these swelled water absorbent resin powders 4 may cause the blocking and make the absorption speed lower. Due to this, in the case of the water absorbent resin powder existing regions 5a-1 and 5a-2 are located near the bottom ends 8a of the respective rising flaps 8, when the wearer repeatedly excretes the urine in the decubitus position, the absorption of the urine is blocked by the swelled water absorbent resin powders 4, and the absorbing ability of each of the fiber assembly layers 7A and 7B located near the respective bottom ends 8a cannot be used any more. This disadvantageously results in leakage of the urine.

The present invention has been achieved to solve the above conventional problems. The purpose of the present invention is to provide a disposable absorbent article that can make effective use of an absorbing ability of the fiber assembly layer located near the bottom ends of the rising flaps, and that can ensure preventing leakage of the urine.

DISCLOSURE OF THE INVENTION

To solve the above-mentioned problems, the invention according to a first embodiment is a disposable absorbent article that includes an absorbent mat between a liquid permeable top sheet and a liquid impermeable back sheet, the absorbent mat including a sheet-like water absorbent layer that contains water absorbent resin powders but does not contain pulp fibers therein, and a fiber assembly layer that mainly consists of the pulp fibers, sequentially from the top sheet side, the sheet-like water absorbent layer including a plurality of water absorbent resin powder existing regions, in each of which the water absorbent resin powders are wrapped in, and a plurality of water absorbent resin powder non-existing regions, in each of which the water absorbent resin powders are not wrapped in, wherein the rising flaps are respectively provided on both lateral ends of the sheet-like water absorbent layer, and each of the bottom ends of the rising flaps is respectively bonded to the top sheet corresponding to the water absorbent resin powder non-existing regions.

The invention according to a second embodiment is a disposable absorbent article that includes an absorbent mat between a liquid permeable top sheet and a liquid impermeable back sheet, the absorbent mat including a sheet-like water absorbent layer that contains water absorbent resin powders but does not contain pulp fibers therein, and a fiber assembly layer that contains the water absorbent resin powders and the pulp fibers, sequentially from a top sheet side, the sheet-like water absorbent layer alternately including a plurality of water absorbent resin powder existing regions, in each of which the water absorbent resin powders are wrapped in, and a plurality of water absorbent resin powder non-existing regions, in each of which the water absorbent resin powders are not wrapped in, in a width direction, wherein the sheet-like water absorbent layer includes rising flaps on both sides thereof, respectively, and each of bottom ends of the respective rising flaps are bonded to the top sheet corresponding to one of the water absorbent resin powder non-existing regions of the sheet-like water absorbent layer.

BEST MODE FOR CARRYING OUT THE INVENTION

Figure 1:
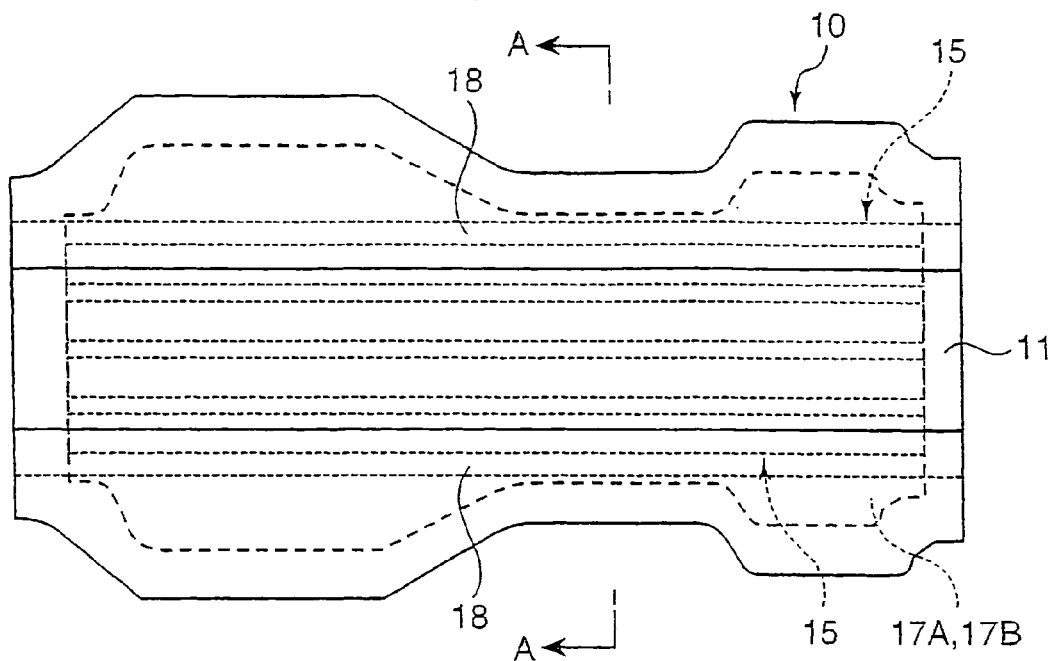
FIG. 1 is a plan view of a disposable absorbent article according to the present invention.

In a disposable absorbent article according to the present invention, the bottom ends of the rising flaps are bonded to the top sheet corresponding to the water absorbent resin powder non-existing regions of the sheet-like water absorbent layer so that water absorbent resin powder existing region near the bottom ends of the respective rising flaps does not exist any more, and only the fiber assembly layers can exist near those. It is, therefore, possible to make effective use of the absorbing ability of the fiber assembly layer located near the bottom end of each rising flap even when the wearer is in the decubitus position, and thereby possible to ensure preventing leakage of urine at the time of excretion of the urine.

Furthermore, since the disposable absorbent article according to the present invention has a high absorbing performance, it is possible to suppress the backflow of the urine to a low level and keep the skin of the wearer clean without staining the skin, even when the wearer uses the article for a long time.

The fiber assembly layer according to the first embodiment of the present invention is configured to mainly consist of the pulp fibers, whereas the fiber assembly layer according to second embodiment of the present invention is configured to contain the water absorbent resin powders and the pulp powders. The point is that the pulp fibers are hydrophilic, and can rapidly absorb the body fluid, therefore the absorbent resin powders are not indispensable. However, the presence of the absorbent resin powders is more preferable because the existence of the absorbent resin powders makes the absorbing capacity of the fiber assembly layer increase, therefore it can prevent the backflow of the urine more effectively.

The sheet-like water absorbent layer according to the second embodiment is configured to alternately include the water absorbent resin powder existing regions and the water absorbent resin powder non-existing regions in the width direction, whereas the sheet-like water absorbent layer according to claim 1 is configured to include the water absorbent resin powder existing regions and the water absorbent resin powder non-existing regions. This means that it is unnecessary to alternately include the water absorbent resin powder existing regions and the water absorbent resin powder non-existing regions in the width direction. However, it is more preferable that the sheet-like water absorbent layer alternately includes the water absorbent resin powder existing regions and the water absorbent resin powder non-existing regions in the width direction, because the sheet-like water absorbent layer can be manufactured more easily when the sheet-like water absorbent layer alternately includes the water absorbent resin powder existing regions and the water absorbent resin powder non-existing regions in the width direction. In addition, even when the sheet-like water absorbent layer repeatedly absorbs the urine or the like, it is possible to prevent the backflow of the urine more effectively while maintaining the absorbing ratio thereof.

The invention according to a further embodiment is the disposable absorbent article according to the first and second embodiments described herein, wherein, if a size between the bottom ends of the respective rising flaps is X, and a size between the water absorbent resin powder existing regions closest to the water absorbent resin powder non-existing regions located on both lateral ends of the sheet-like water absorbent layer, respectively is Y, the X and the Y hold a size relationship represented by Y=0.2X to 0.9X, and in that if a horizontal size from the outermost edge of the above water absorbent resin powder existing region to the neighboring bottom end of each of the rising flaps is Z, the X and the Z hold a size relationship represented by Z=0.05X to 0.4X The best mode for carrying out the present invention will be described hereinafter in detail with reference to the drawings.

Figure 2:
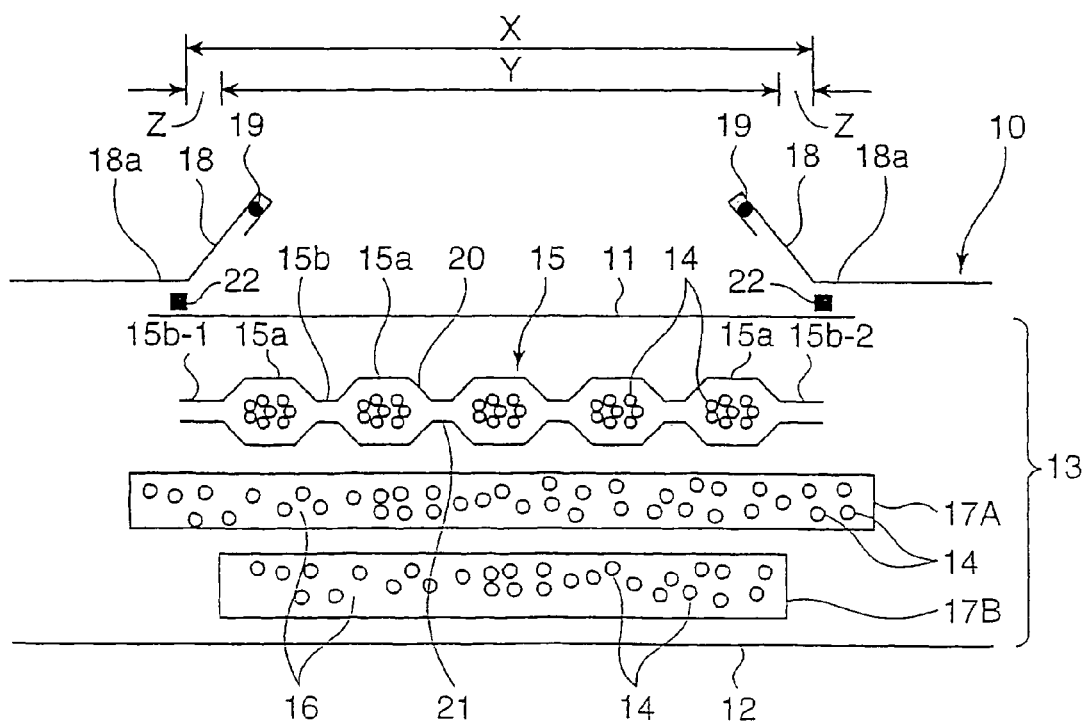
FIG. 2 is a cross-sectional view taken along a line A-A of FIG. 1.
Figure 3:
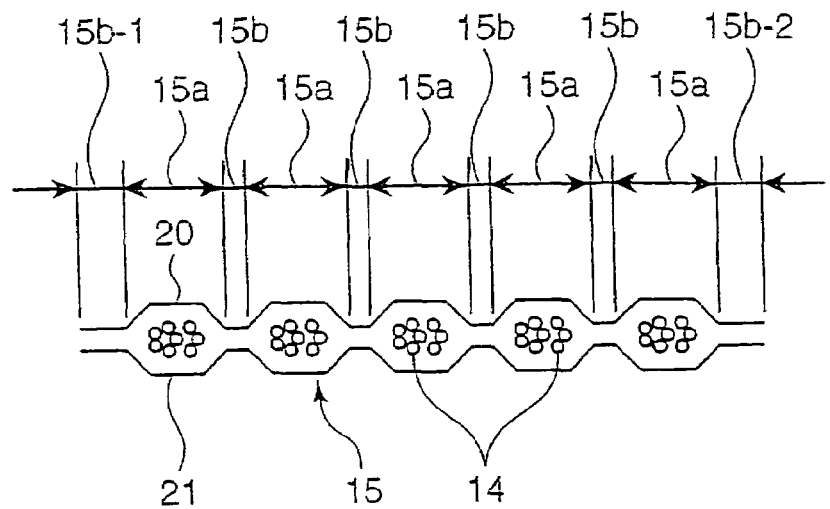
FIG. 3 is a cross-sectional view of a sheet-like absorbent layer.

FIG. 1 is a plan view of a disposable absorbent article 10;
FIG. 2 is a cross-sectional view taken along a line A-A of FIG. 1; and FIG. 3 is a cross-sectional view of a sheet-like water absorbent layer 15.

The disposable absorbent article 10 includes an absorbent mat 13 between a liquid permeable top sheet 11 and a liquid impermeable back sheet 12. The absorbent mat 13 includes a sheet-like water absorbent layer 15 that contains water absorbent resin powders 14 but does not contain pulp fibers therein, and fiber assembly layers 17A and 17B each of which includes the pulp fibers 16, sequentially from a top sheet 11 side.

In the sheet-like water absorbent layer 15, the water absorbent resin powders 14 are held between the first non-woven fabric sheet 20 and the second non-woven fabric sheet 21, and the water absorbent resin powders 14 are fixed to the first non-woven fabric sheet 20 and the second non-woven fabric sheet 21 with an adhesive. In addition, the sheet-like water absorbent layer 15 is designed not to contain the pulp fibers 16.

The sheet-like water absorbent layer 15 alternately includes a plurality of water absorbent resin powder existing regions 15a, in each of which the water absorbent resin powders 14 are wrapped in, and a plurality of water absorbent resin powder non-existing regions 15b, in each of which the water absorbent resin powders 14 are not wrapped in, in a width direction. The first non-woven fabric sheet 20 and the second non-woven fabric sheet 21 are bonded to each other in each water absorbent resin powder non-existing region 15b to thereby seal the water absorbent resin powder non-existing region 15b. Namely, by sealing a water absorbent resin powder non-existing region 15b, the water absorbent resin powder existing region 15a is partitioned from the adjacent water absorbent resin powder existing region 15a thereof, respectively.

The first non-woven fabric sheet 20 and the second non-woven fabric sheet 21 consist of liquid permeable non-woven fabrics, respectively. As fibers that constitute such non-woven fabrics, hydrophilic fibers such as cellulose, rayon, or cotton fibers, as well as hydrophobic fibers, which are surface-treated to obtain hydrophilicity with surfactant, such as polypropylene, polyethylene, polyester, or polyamide fibers are available.

As a resin used for the water absorbent resin powders 14, for instance, a water absorbent resin can be listed, such as polyacrylic acid (salt), cellulose, starch, and acrylonitrile. An application amount of the water absorbent resin powders 14 is preferably equal to or higher than 100 $g/m^2$ and equal to or smaller than 250 $g/m^2$ relative to each existing region. The water absorbent resin powders 14 are not limited to be a powdery material but a fibrous material can also be used.

The fiber assembly layers 17A and 17B are two layers provided below the sheet-like water absorbent layer 15 and intended to secure an amount of absorption that enables long-time use. Alternatively, the number of the fiber assembly layers can be one.

Each of the fiber assembly layers 17A and 17B mainly consists of the pulp fibers 16 and the water absorbent resin powders 14 dispersed therein, and is formed by integrating the pulp fibers 16 and the water absorbent resin powders 14, and then is wrapped up with a thin paper (e.g., a tissue paper).

As the pulp fibers 16 that form the fiber assembly layer, well-known defibrated pulp can be used. The fiber assembly layer can also contain heat-sealable fibers to improve shape retaining ability. Examples of such heat-sealable fibers include polyolefin fibers consisting of polyethylene or polypropylene, polyester fibers, and composite fibers thereof.

As the water absorbent resin powders 14 dispersed in the fiber assembly layers 17A and 17B, the same powders as those contained in the sheet-like water absorbent layer 15 can be used. An amount of the water absorbent resin is preferably equal to or higher than 15 mass %, and equal to or lower than 90 mass % relative to an amount of the pulp fibers used in the fiber assembly layer.

An entire plane shape of the fiber assembly layers 17A and 17B can be appropriately determined according to purposes, and can be, for instance, gourd-shaped, rectangular or hourglass-shaped.

Rising flaps 18 are provided on both sides of the sheet-like water absorbent layer 15, respectively. Bottom ends 18a of the rising flaps 18 are bonded to the top sheet 11 corresponding to the water absorbent resin powder non-existing regions 15b-1 and 15b-2 located on both lateral ends of the sheet-like water absorbent layer 15, respectively, with an adhesive 22 or the like.

Rising elastic members 19 are provided in and extended longitudinally along the upper ends of the above rising flaps 18.

As a material for the rising flaps 18, it is preferable to use a water-repellant sheet material or a liquid impermeable sheet material. More preferably, water-repellant non-woven fabrics consisting of the heat-sealable fibers such as spunbond non-woven fabrics, melt-blown non-woven fabrics, or SMS non-woven fabrics, an air-permeable or air-impermeable plastic film (even more preferably air-permeable plastic film), or a composite material thereof can be used.

Under the situation that the disposable absorbent article 10 is configured as mentioned above by bonding the bottom ends 18a of the rising flaps 18 to the top sheet 11 corresponding to the water absorbent resin powder non-existing regions 15b-1 and 15b-2 on the both lateral ends of the sheet-like water absorbent layer 15 respectively, the water absorbent resin powder existing regions 15a are not present but only the fiber assembly layers 17A and 17B are present near the bottom ends 18a of the rising flaps 18. It is, therefore, possible to make effective use of the absorbing ability of each of the fiber assembly layers 17A and 17B located near the bottom ends 18a of the respective rising flaps 18 even when the wearer is in the decubitus position. It is thereby possible to ensure preventing leakage of urine at the time of excretion of the urine. In addition, the absorbent resin powders 14 may be unevenly provided so that the powders 14 are not present in the portions of the fiber assembly layers 17A and 17B located near the bottom ends 18a. This can also prevent the absorbent resin powders 14 from being swelled so as not to hamper repeated absorption of the urine or the like.

Since the disposable absorbent article 10 has a high absorbing performance, even when the wearer uses the article for a long time, it is possible to suppress the backflow of the urine or the like to a low level and keep the skin of the wearer clean without staining the skin.

Moreover, it is preferable to ensure preventing the leakage of the urine or the like that if a size between the bottom ends 18a of the respective rising flaps 18 is X and a size between the water absorbent resin powder existing regions 15a closest to the water absorbent resin powder non-existing regions 15b-1 and 15b-2 located on both lateral ends of the sheet-like water absorbent layer 15, respectively is Y, the X and the Y hold a size relationship represented by Y=0.2X to 0.9X, and that if a horizontal size from the outermost edge of the above water absorbent resin powder existing region 15a to the neighboring bottom end 18a of each of the rising flaps 18 is Z, the X and the Z hold a size relationship represented by Z=0.05X to 0.4X.

Figure 4:
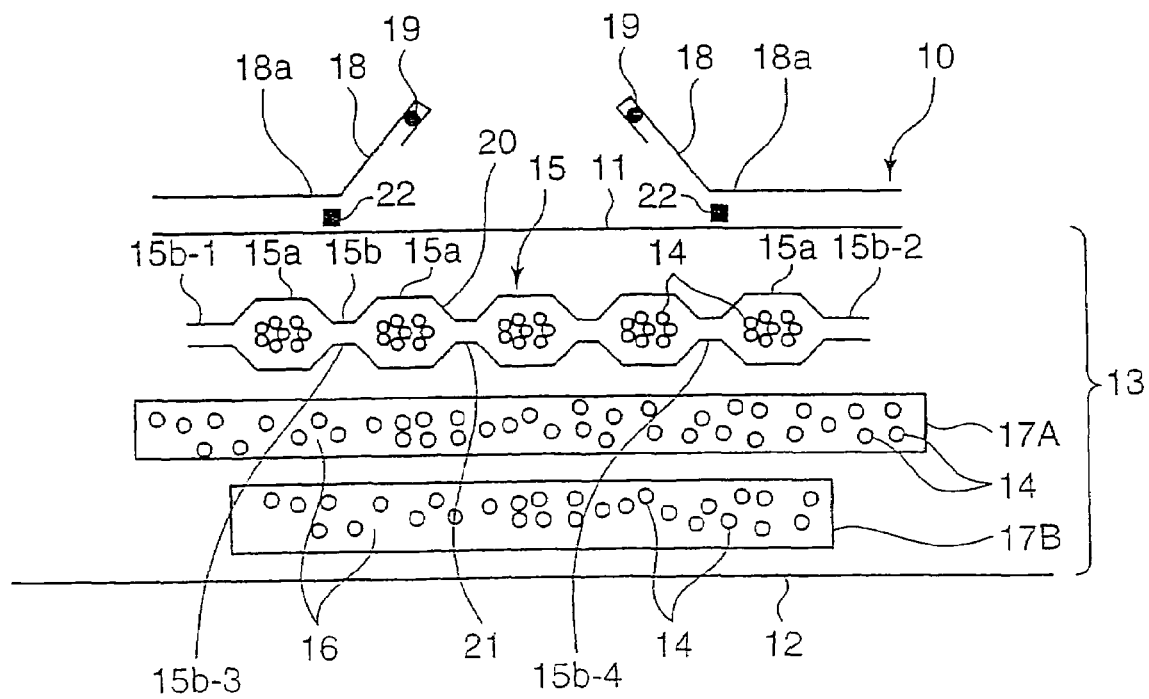
FIG. 4 is a cross-sectional view of a disposable absorbent article according to a modified embodiment, which corresponds to the cross-sectional view taken along the line A-A of FIG. 1.
Figure 5:
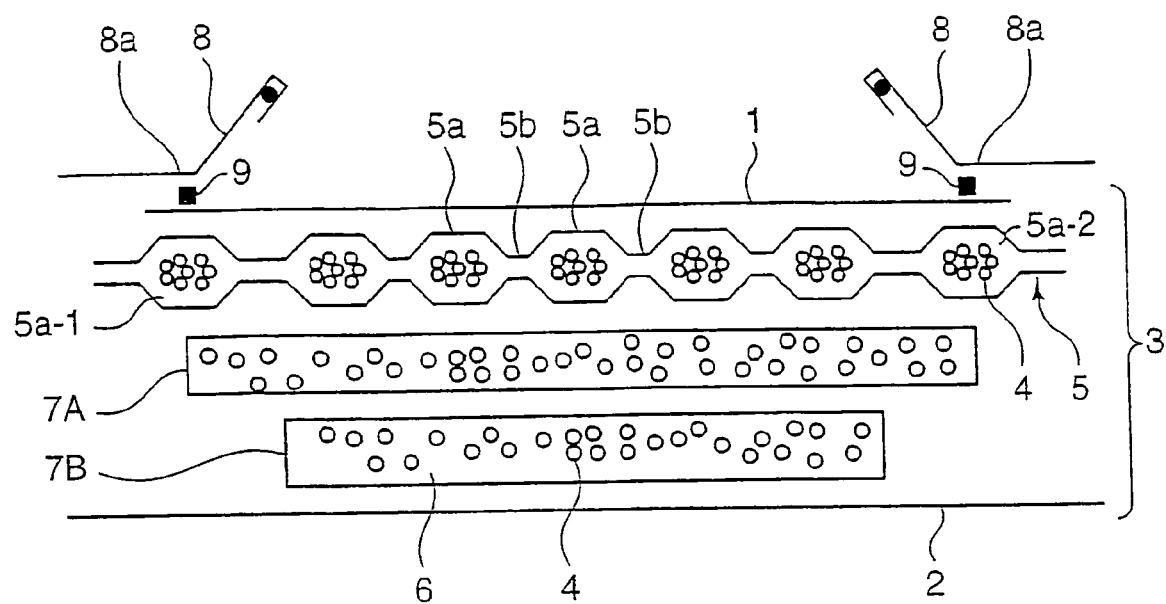
FIG. 5 is a cross-sectional view of a disposable absorbent article according to a conventional technique.

FIG. 4 depicts a modified embodiment. In the above-stated embodiment, the bottom ends 18a of the rising flaps 18 are bonded to the top sheet 11 corresponding to the water absorbent resin powder non-existing regions 15b-1 and 15b-2 located on both lateral ends of the sheet-like water absorbent layer 15, respectively, with the adhesive 22 or the like. To the contrary, in this modified embodiment, the bottom ends 18a of the rising flaps 18 are bonded to the top sheet 11 corresponding to the water absorbent resin powder non-existing regions 15b-3 and 15b-4 located just inward of the water absorbent resin powder existing regions 15a located on the both lateral ends of the sheet-like water absorbent layer 15, respectively, with the adhesive 22 or the like. This modified embodiment can exhibit the same functions and advantages as those of the above-stated embodiment.

INDUSTRIAL APPLICABILITY

The disposable absorbent article according to the present invention can ensure preventing leakage of the urine during excretion of the urine and has a high absorbing performance. Therefore, even when the article is used for a long time, it is possible to suppress backflow of the urine to a low level, and keep the skin of the wearer clean without staining the skin. This disposable absorbent article can be, therefore, used as a disposable diaper, disposable pants or the like.

The invention claimed is:

1. A disposable absorbent article, comprising:
a liquid permeable top sheet and a liquid impermeable back sheet; and
an absorbent mat being disposed between said liquid permeable top sheet and said liquid impermeable back sheet, the absorbent mat including a water absorbent layer that contains water absorbent resin powders but that does not contain pulp fibers therein and a fiber assembly layer that contains the pulp fibers and the water absorbent resin powders dispersed therein, sequentially from a top sheet side, the water absorbent layer including water absorbent resin powder existing regions, in each of which the water absorbent resin powders are wrapped between a first non-woven fabric sheet and a second non-woven fabric sheet, and water absorbent resin powder non-existing regions, in each of which the first non-woven fabric sheet and the second non-woven fabric sheet are bonded to each other to partition the water absorbent resin powder existing region from an adjacent water absorbent resin powder existing region respectively, wherein,
the water absorbent resin powder existing regions and the water absorbent resin powder non-existing regions are alternately disposed in a width direction, and
rising flaps are respectively provided on both lateral ends of the water absorbent layer, and each of bottom ends of the rising flaps are respectively bonded to the top sheet in a position corresponding to the water absorbent resin powder non-existing regions.

2. The disposable absorbent article according to claim 1, wherein,
provided that a size between the bottom ends of the respective rising flaps is X and a size between the water absorbent resin powder existing regions closest to the water absorbent resin powder non-existing regions located on both lateral ends of the water absorbent layer, respectively is Y, the X and the Y hold a size relationship represented by Y=0.2X to 0.9X, and provided that a horizontal size from outermost edge of the water absorbent resin powder existing region to the neighboring bottom end of each of the rising flaps is Z, the X and the Z hold a size relationship represented by Z=0.05X to 0.4X.

3. The disposable absorbent article according to claim 1, wherein
- each of the water absorbent resin powder existing regions extends in a longitudinal direction along an entire length of the water absorbent layer, and
- each of the water absorbent resin powder non-existing regions extends in a longitudinal direction along the entire length of the water absorbent layer.

4. The disposable absorbent article according to claim 1, wherein the water absorbent resin powders are fixed to the first non-woven fabric sheet and the second non-woven fabric sheet with an adhesive.

5. The disposable absorbent article according to claim 1, wherein the fiber assembly layer is formed by integrating the water absorbent resin powders and the pulp fibers.

6. The disposable absorbent article according to claim 1, wherein the fiber assembly layer is wrapped with a thin paper.

7. The disposable absorbent article according to claim 1, wherein the amount of the water absorbent resin powder in the water absorbent resin powder existing region is equal to or higher than 100 $g/m^2$ and equal to or smaller than 250 $g/m^2$.

8. The disposable absorbent article according to claim 1, wherein the amount of the water absorbent resin in the fiber assembly layer is equal to or higher than 15 mass % and equal to or lower than 90 mass % relative to the amount of the pulp fibers.

* * * * *